(12) United States Patent
Carucci et al.

(10) Patent No.: US 11,717,486 B2
(45) Date of Patent: Aug. 8, 2023

(54) HIGHLY STABLE FORMULATIONS OF THYROID HORMONE IN SOFT CAPSULES

(71) Applicant: ALTERGON S.A., Lugano (CH)

(72) Inventors: Simone Carucci, Lugano (CH); Maurizio Marchiorri, Lugano (CH); Marco Pontiggia, Lugano (CH); Tiziano Fossati, Lugano (CH)

(73) Assignee: ALTERGON S.A., Lugano (CH)

( * ) Notice: Subject to any disclaimer, the term of this patent is extended or adjusted under 35 U.S.C. 154(b) by 234 days.

(21) Appl. No.: 16/970,694

(22) PCT Filed: Mar. 6, 2019

(86) PCT No.: PCT/EP2019/055547
§ 371 (c)(1),
(2) Date: Aug. 18, 2020

(87) PCT Pub. No.: WO2019/174990
PCT Pub. Date: Sep. 19, 2019

(65) Prior Publication Data
US 2020/0375909 A1    Dec. 3, 2020

(30) Foreign Application Priority Data
Mar. 15, 2018    (IT) .................. 102018000003615

(51) Int. Cl.
*A61K 9/48* (2006.01)
*A61K 31/198* (2006.01)
*A61K 47/36* (2006.01)

(52) U.S. Cl.
CPC ............. *A61K 9/4866* (2013.01); *A61K 9/485* (2013.01); *A61K 9/4825* (2013.01); *A61K 9/4858* (2013.01); *A61K 31/198* (2013.01); *A61K 47/36* (2013.01)

(58) Field of Classification Search
None
See application file for complete search history.

(56) References Cited

U.S. PATENT DOCUMENTS

| | | |
|---|---|---|
| 5,958,979 A | 9/1999 | Lahr et al. |
| 6,214,376 B1 * | 4/2001 | Gennadios ........... A61K 9/4816 424/452 |
| 7,723,390 B2 | 5/2010 | Garavani et al. |
| 2004/0087669 A1 * | 5/2004 | Hausmanns ......... A61K 9/4816 516/99 |

FOREIGN PATENT DOCUMENTS

WO    2004043140 A2    5/2004

OTHER PUBLICATIONS

International Search Report and Written Opinion for Corresponding International Application No. PCT/EP2019/055547 (9 Pages) (May 8, 2019).

* cited by examiner

*Primary Examiner* — Nannette Holloman
(74) *Attorney, Agent, or Firm* — Lucas & Mercanti, LLP

(57) ABSTRACT

New soft capsules are described having within them a fill which contains thyroid hormones such as thyroxine T4 or triiodothyronine T3) and a high amylose-starch, optionally associated with vegetable hydrocolloids and/or glycerol. Compared to traditional capsules, these capsules have a strong and unexpected increase in the stability of T4 or T3 during storage.

16 Claims, No Drawings

HIGHLY STABLE FORMULATIONS OF THYROID HORMONE IN SOFT CAPSULES

CROSS-REFERENCE TO RELATED APPLICATIONS

This application is a 371 of PCT/EP2019/055547, filed Mar. 6, 2019, which claims the benefit of Italian Patent Application No. 102018000003615, filed Mar. 15, 2018.

FIELD OF THE INVENTION

The present invention relates to the field of pharmaceutical compositions in soft capsules containing active ingredients of hormonal nature and stable for storage.

BACKGROUND OF THE INVENTION

Soft capsules are a pharmaceutical form widely used for active ingredients that need to be formulated in a liquid or semi-liquid state, but which are poorly soluble in water; the use of this pharmaceutical form is ideal in the case of active ingredients at very low unit doses: in this case the formulation in solution is preferable to the solid one as it allows a more uniform distribution of the active ingredient in the liquid vehicle, to the advantage of a better dosing accuracy. Furthermore, the formulation of the active ingredient in a liquid vehicle facilitates the dispersion and absorption of the drug after the capsular wall has been degraded by the body's liquids. Soft capsules can also be used for water-soluble active ingredients, exploiting in this case other properties, in particular, the activity of masking the taste and/or smell of the active ingredient, the easy deglutition, etc.

Soft capsules have a sealed outer envelope and, within them, a liquid or pasty fill, within which the active ingredient is dissolved or dispersed. For a review, see e.g. Gullapalli et al., *J. Pharmaceutical Sciences,* 99 (10), 2010, 4107).

The term "soft capsules" used herein means capsules whose outer shell (capsular wall) comprises animal gelatine and/or vegetable hydrocolloids; the term "soft capsules" is also referring herein, in agreement with the *European Pharmacopoeia* 9.3, p. 4783, to sealed capsules, whose interior contains a semi-solid or liquid preparation.

Thyroid hormones are among those active ingredients that can be formulated in soft capsules. They predominantly consist of thyroxine (also known as tetraiodothyronine or T4 hormone) and, to a lesser extent, triiodothyronine (T3 hormone). The thyroid hormones perform multiple biological functions. In the absence of these hormones (hypothyroidism), all the metabolic activities slow down: the heart rate is reduced (bradycardia), the basal metabolic rate decreases, the intestine becomes lazy (constipation), the muscles become torpid, and the mental activities slow down. This generalized metabolic slowdown results in an increase in body weight, with retention of water and mucopolysaccharides. This particular type of edema is called myxoedema or gelatinous edema or mixed edema, precisely because it consists of water and mucopolysaccharides (glycosaminoglycans and hyaluronic acid).

Those suffering from hypothyroidism must resort to external intake of thyroxine or triiodothyronine, whose primary action is to accelerate cell metabolism, resulting in heat production. Furthermore, thyroxine and triiodothyronine promote cholesterol metabolism (hypothyroidism states are associated with hypercholesterolemia); they also increase the use of carbohydrates and the rate of intestinal glucose absorption, counteracting the aggravation of the aforementioned symptoms in hypothyroid subjects.

Besides hypothyroidism in all its forms (e.g. primary, secondary, and tertiary) and to the myxedema, further non-limiting examples of pathologies or physiological conditions addressed by the present invention requiring the administration of thyroid hormones such as thyroxine and/or triiodothyronine, are: thyroid nodules, thyroid cancer, goiter and hashimoto thyroiditis.

In order for thyroxine and triiodothyronine to act correctly, it is of fundamental importance that they maintain their structural characteristics unchanged during their storage in the soft capsules that will then be administered to the patients. It is well known that there is a close correlation between the structure of the hormone and its functionality.

It is also known that thyroxine and triiodothyronine are chemically unstable compounds, because they are affected by heat, light, air exposure and humidity. This phenomenon is critical when thyroxine or triiodothyronine are inserted into soft capsules. In fact, these capsules have a certain permeability to oxygen and a propensity to absorb moisture from the environment, as well as having their own percentage of water, both in the capsular wall and inside the fill. These factors may favour the degradation of thyroxine or triiodothyronine, leading to an undesired reduction in their titre and the possible formation of impurities. It should be added that thyroxine and triiodothyronine are effective at extremely low doses, therefore an even moderate reduction of the titre may result in significant reductions in the therapeutic efficacy.

The Applicant in U.S. Pat. No. 7,723,390 describes a soft capsule formulation wherein said critical factors are kept under control with the appropriate formulation described therein.

Therefore, there is a need for improved formulations of thyroxine or triiodothyronine, specifically designed to protect these hormones, particularly when they are present in pharmaceutical forms particularly exposed to environmental factors, such as soft capsules.

SUMMARY

It has now unexpectedly been found that a specific starch-based excipient, i.e. high-amylose starch, when incorporated into the fill of a soft capsule together with thyroxine or triiodothyronine, possibly in the presence of further vegetable hydrocolloids, and/or glycerol, shows a particular and unexpected stabilizing activity of thyroxine and triiodothyronine. Therefore, the invention is directed to a soft capsule having internally a fill comprising thyroxine (T4 hormone) or triiodothyronine (T3 hormone), a high-amylose starch, preferably in association with one or more vegetable hydrocolloids and/or glycerol. The invention further includes a process for preparing said capsules and the use thereof in the treatment of diseases or physiological conditions requiring the administration of thyroid hormones.

DETAILED DESCRIPTION OF THE INVENTION

The expression "high amylose-starch" used herein, means a starch containing about: at least 50%, preferably from 50 to 85%, more preferably between 65 and 75%, e.g. about 70% by weight of amylose with respect to the total weight of starch, wherein the term "about" indicates a variability of ±3%. A preferred class of high-amylose starches useful for the purposes of the invention is commercially available under the trademark Hylon®, e.g. Hylon VII. High-amylose starch was unexpectedly found by the present Applicant to preserve the stability of thyroid hormones in liquid or semi-liquid phase, in particular in the fill of soft gelatine capsules; this ingredient is seldom used in pharmaceutical technology (cf. e.g. WO2004/043140, showing its use as binder for slow-release pharmaceutical microparticles (cf.); high-amylose starch differs significantly from standard starches which contain less than 30% amylose, the remainder being amylopectin; for example, the following amounts of amylose are reported for starches: wheat (25%), barley (19-22%), rice 21-25%), corn (28%), potato (29%), etc.; standard starches are generally used as binders in solid pharmaceutical forms (cf. e.g. U.S. Pat. No. 5,958,979).

The term "hydrocolloid" refers to a substance which, in the presence of water, is in the colloidal state, i.e. a system formed by a dispersing phase (water) and a dispersed phase (typically polysaccharide molecules forming fibers or other aggregated structures capable of retaining water molecules); this colloidal state may be in the form of a hydrosol, a viscous liquid and a hydrogel, depending on its water content.

The term "vegetable", used in relation to hydrocolloids, generally identifies all non-animal hydrocolloids; it is inclusive of hydrocolloids of microbiological origin, as well as semi-synthetic hydrocolloids obtained from vegetable sources. Examples of vegetable hydrocolloids are galactomannans (guar, carob, tara, konjac, etc.), alginates, carrageenans, xanthans, carboxymethylcellulose, hydroxypropyl cellulose, hydroxypropyl methylcellulose, agar-agar, gellan. Carrageenans and xanthans are particularly preferred according to the invention.

Thyroxine (T4) and triiodothyronine are used in all their available forms, in particular in the form of the levorotatory isomer (levothyroxine and levotriiodothyronine); they can be used as such or as pharmaceutically acceptable salts, e.g. sodium salt: the terms "thyroxine" or "T4" and "triiodothyronine" or "T3" used herein are understood to include all these forms.

According to a preferred embodiment, within the fill of the present capsules, the high-amylose starch content is between 10 and 50% by weight, preferably 15-45% by weight, on the weight of the fill. According to a preferred embodiment, the T4 or T3 hormones and the high-amylose starch are formulated in the fill in association with the carrageenan and/or xanthan hydrocolloids.

Carrageenan is a polysaccharide widely used in the food, medicine and industry fields. According to a particularly preferred embodiment, the content of carrageenan in the fill is between 0.05 and 5% by weight, preferably 0.2-3% by weight, on the weight of the fill.

Xanthan (also known as xanthan gum) is a polysaccharide used as a food additive and rheological modifier. It is obtained by the fermentation process in pure culture of a carbohydrate (glucose or sucrose) by natural strains of the bacterium *Xantomonas campestris*, purified by extraction with ethanol or 2-propanol, dried and ground. It contains D-glucose and D-mannose as main hexoses, as well as D-glucuronic and pyruvic acids, and is prepared as sodium, potassium or calcium salts. According to a preferred embodiment, the content of the xanthan in the fill is in the range 0.03-3% by weight, preferably 0.05-2%, or 0.1-2% by weight, on the weight of the fill.

The fill of the present capsule may also contain glycerol. According to a preferred embodiment, the glycerol content in the fill is in the range 12-45% by weight, on the weight of the fill. For the purposes of the aforementioned amounts and ratios by weight, "glycerol" means herein an 85% by weight aqueous solution of glycerol (typical form of glycerol for pharmaceutical use). This does not exclude the use of other forms of glycerol for the purposes of the invention, providing glycerol amounts equivalent to those set forth herein.

In addition to the aforesaid characteristic ingredients, the fill may optionally include other ingredients commonly used in the preparation of soft capsule fills; these ingredients and their non-critical amounts according to the invention can be selected according to the common knowledge of the art.

The composition of the wall of the present capsules is not particularly critical and may comprise ingredients commonly used in the production of soft capsules, in particular, gelatin or vegetables hydrocolloids, water, plasticizers, opacifiers, dyes, flavorings, etc.

A further object of the invention is a process for preparing a soft capsule, said process comprising coating a fill comprising T4 or T3 and high-amylose starch, as described above, with a gelatin- and/or vegetable hydrocolloid-based capsular wall. Apart from the use of the characteristic fill of the present invention, the preparation process of the capsules does not present any further criticality. It comprises, in its general form: (i) preparing a fill composition as described above, dividing said composition into discrete units, coating said units with a solution of the components of the capsular wall, drying the resulting product, thus obtaining the soft capsules according to the invention. The preparation of the fill preferably comprises a homogeneous dispersion of its constituents, so as to maximize the contact between T4 or T3, high-amylose starch and any hydrocolloids present. The dispersion of the fill components can be obtained by known means and methods, for example stirring, extrusion, etc. The division of the fill composition into discrete units, their coating with the solution of the capsular wall components and the final drying take place equally by known techniques.

The capsules made according to the invention are suitable to contain amounts of T4 or T3 useful for the therapeutic administration to a patient in need. A further aspect of the invention is a soft capsule as described herein for use in the treatment and/or prevention of diseases related to thyroid hormone deficiency.

The invention is hereinafter described by means of some non-limiting examples.

EXPERIMENTAL

Formulations

Two different fills have been made according to the invention, to test the stability of the levothyroxine stored therein.

The first fill consisted of levothyroxine (T4), glycerol, water, high-amylose starch (Hylon VII) and xanthan gum; the second, instead, consisted of levothyroxine (T4), glycerol, water, high-amylose starch (Hylon VII), and carrageenan.

The aforementioned fills have been formulated as follows, wherein the amounts of each compound are expressed as percentages by weight with respect to the total weight of the capsule fill.

| First fill composition according to the invention | |
|---|---|
| Batch 001H17-079 | % |
| Hylon VII | 38 |
| Glycerin 85% | 36 |
| Xanthan gum | 0.3 |
| Water | 25.567 |
| T4 | 0.133 |

| Second fill composition according to the invention | |
|---|---|
| Batch 002H17-079 | % |
| Hylon VII | 38 |
| Glycerin 85% | 36 |
| Carrageenan Sol CPA 5919 | 0.52 |
| Water | 25.347 |
| T4 | 0.133 |

In order to compare the stability results of levothyroxine in the capsule fills according to the invention with respect to those obtained with a generic fill, a third type of fill was also provided, characterized in that the high-amylose starch and the vegetable hydrocolloids were replaced by gelatin (animal hydrocolloid).

The aforesaid fill has been formulated as follows, wherein the amounts of each compound are expressed as a percentage by weight with respect to the total weight of the capsule fill.

| Standard fill composition | |
|---|---|
| Batch 005H17-079 | % |
| Hydrolyzed gelatin | 35 |
| Gelatin 80 bloom | 5 |
| Glycerol 85% | 35 |
| Water | 24.867 |
| T4 | 0.133 |

Analytical Results

Three different types of capsules were prepared for each of the 3 above mentioned fill compositions respectively, and the stability of levothyroxine was assessed in each of the three capsules at the beginning of the test (starting time), after 7 days, after 14 days, after 21 days, and after 28 days from the starting time, at a constant temperature of 50° C. (stress test).

The results are summarized in the tables below.

| First fill composition according to the invention | | | | |
|---|---|---|---|---|
| Sample: Batch 001H17-079 | Starting time (%) | 7 days 50° C. (%) | 14 days 50° C. (%) | 28 days 50° C. (%) |
| T4 Titre % imp with respect to T4 | 99.18 | 97.9 | 96.71 | 97.08 |
| Max unknown | 0.34 | 0.41 | 0.37 | 0.47 |
| total unknown | 1.33 | 2.77 | 1.72 | 2.33 |

-continued

| First fill composition according to the invention | | | | |
|---|---|---|---|---|
| Sample: Batch 001H17-079 | Starting time (%) | 7 days 50° C. (%) | 14 days 50° C. (%) | 28 days 50° C. (%) |
| T3 | 0.32 | 0.69 | 0.75 | 0.86 |
| Triac | 0.05 | 0.08 | 0.06 | 0.06 |
| total: | 1.71 | 3.54 | 2.54 | 3.26 |

| Second fill composition according to the invention | | | | |
|---|---|---|---|---|
| Sample: Batch 002H17-079 | Starting time (%) | 7 days 50° C. (%) | 14 days 50° C. (%) | 28 days 50° C. (%) |
| T4 Titre % imp with respect to T4 | 98.96 | 104.43 | 107.37 | 100.36 |
| Max unknown | 0.31 | 0.46 | 0.43 | 0.49 |
| total unknown | 1.49 | 2.24 | 2.12 | 2.41 |
| T3 | 0.34 | 0.79 | 0.96 | 1.23 |
| Triac | 0.07 | 0.06 | 0.08 | 0.08 |
| total: | 1.71 | 3.10 | 3.16 | 3.72 |

| Standard fill composition | | | | |
|---|---|---|---|---|
| Sample: Batch 005H17-079 | Starting time (%) | 7 days 50° C. (%) | 14 days 50° C. (%) | 28 days 50° C. (%) |
| T4 Titre % imp with respect to T4 | 102.57 | 79.36 | nd | 35.69 |
| Max unknown | 0.33 | 0.23 | nd | 1.01 |
| total unknown | 1.45 | 1.07 | nd | 1.95 |
| T3 | 0.38 | 16.73 | nd | 44.54 |
| Triac | 0.08 | 0.09 | nd | 0.08 |
| total: | 1.90 | 17.80 | nd | 46.57 | wherein:

Titre: levothyroxine titre

% imp. with respect to T4: percentage impurities compared to T4

Max unknown: maximum unknown impurity

T3: triiodothyronine

Triac: 3,3',5-triiodothyroacetic acid

The stability tests showed a clear stability for the new capsules (initial T4 titre substantially unchanged at 100% after 28 days at 50° C.); on the contrary, the reference capsules underwent a dramatic reduction of the titre up to 35%. It is therefore evident that the fill compositions of the soft capsules made according to the present invention have produced a marked increase in stability of the T4 hormone.

Further Comparative Tests

A further test was carried out to verify if the stabilizing effect of T4 by the high-amylose starch was maintained when said starch was not present in the fill but in the capsular wall (shell). Two batches of soft capsules having the same composition were then prepared, except for the presence/absence of Hylon VII in the capsular wall:

|  | With Hylon VII mg/cps | Standard Formulation mg/cps |
|---|---|---|
| Fill | | |
| Sodium Levothyroxine | 0.100 | 0.100 |
| Hydrolyzed gelatin | 26.250 | 26.250 |
| Gelatin 80 bloom pigskin | 3.750 | 3.750 |
| Glycerol 85% | 26.250 | 26.250 |
| Purified water | 18.650 | 18.650 |
| Sodium hydroxide | 0.006 | 0.006 |
| Shell | | |
| Gelatin 150 bloom | 85.000 | 97.500 |
| Anhydrous glycerol | 57.500 | 57.500 |
| Hylon VII | 12.500 | — |
| Purified water | 95.000 | 95.000 |

Both batches were stored at 40° C. and 75% relative humidity for 6 months. The results obtained are as follows:

|  | T0 | 1 month | 3 months | 6 months |
|---|---|---|---|---|
| Standard formulation | | | | |
| T4 | 99.6 | 98.2 | 93.6 | 87.5 |
| T3 | 0.43 | 1.21 | 2.92 | 5.77 |
| T3 reverse | <LOQ | 0.11 | 0.21 | 0.44 |
| TRIAC | n.a. | n.a. | <LOQ | <LOQ |
| Total unknown impur. | <LOQ | <LOQ | 0.1 | 0.15 |
| Total impurities | 0.43 | 1.32 | 3.23 | 6.36 |
| With Hylon VII | | | | |
| T4 | 98.2 | 96.5 | 93.7 | 87 |
| T3 | 0.49 | 1.17 | 2.47 | 4.96 |
| T3 reverse | <0.08 | <0.08 | <0.08 | 0.13 |
| TRIAC | <0.24 | <0.24 | <0.24 | <0.24 |
| Total unknown impur. | 0.44 | 0.34 | 0.49 | 0.35 |
| Total impurities | 1.47 | 2 | 3.39 | 6.02 |

The data show for the two formulations a substantially identical stability profile, i.e. the addition of high-amylose starch to the capsular wall did not increase the stability of the T4 hormone. It is therefore confirmed that, in order to increase the stability of the T4 hormone, it is important to formulate the high-amylose starch in the fill, together with the T4 hormone, according to the present invention.

A further test was carried out to verify if the increase in stability of T4 was obtained by using, within the fill, hydrocolloids different from high-amylose starch. To this end, a batch of soft capsules containing the T4 hormone in the presence of pectin and gellan gum was prepared. The composition of the capsule was as follows:

| Fill with Pectin and gellan gum | % | Mg/cps | Kg/batch |
|---|---|---|---|
| levothyroxine sodium | 0.100 | 0.075 | 0.0100 |
| hydrolyzed gelatin | 30.000 | 22.500 | 3.0000 |
| bovine gelatin 80 bloom | 4.000 | 3.000 | 0.4000 |
| Glycerol 85% | 26.000 | 19.500 | 2.6000 |
| Pectin CU 401-USP | 1.393 | 1.045 | 0.1393 |
| Gellan rubber | 0.036 | 0.027 | 0.0036 |
| Purified water | 38.471 | 28.853 | 3.8471 |
| total Fill | 100.000 | 75.000 | 10.0000 |

| Fill with Pectin and gellan gum | % | Mg/cps | Kg/batch |
|---|---|---|---|
| Shell | | | |
| Gelatin 150 bloom | 39.00 | 97.50 | 31.20 |
| Anhydrous Glycerol | 23.00 | 57.50 | 18.40 |
| Purified water | 38.00 | 95.00 | 30.40 |
| total shell | 100.00 | 250.00 | 80.00 |

At the same time, a batch of capsules (standard formulation) having the same composition as the one shown above was prepared, but with the difference of not including, within the fill, the pectin+gellan gum association. The stability data for the two batches, after storage for 12 months at 25° C. and 60% relative humidity, are the following:

| 25° C./60% rh | Standard formulation 12 m | With Pectin and gellan gum 12 m |
|---|---|---|
| Appearance | Compliant | Compliant |
| Medium weight | 206 | 214.8 |
| Mass uniformity | Compliant | Compliant |
| Loss on drying | 5.4 | 8.8 |
| Identification T4 | Compliant | Compliant |
| Assay T4 | 98.4 | 96.5 |
| T3 | 1.6 | 1.5 |
| T3 reverse | 0.23 | 0.30 |
| TRIAC | <LOQ | <LOQ |
| Each unknown impur. | 0.15 | 0.1 |
| Total impurities | 2.08 | 1.8 |

These data show for the two formulations a substantially equal stability, i.e. the addition in the fill of hydrocolloids other than high-amylose starch does not result in an increased stability of the T4 hormone. It is therefore confirmed that, to increase the stability of the T4 hormone, it is important to formulate the T4 in the fill with a high-amylose starch, according to the present invention.

Further Formulation Tests

The following are further tests related to the formulation development of fills according to the invention.

|  | % w/w |
|---|---|
| Example 1 | |
| Hylon VII | 41 |
| Slycerin 85% | 35 |
| Xantan gum | 0.25 |
| Water | 23.617 |
| T4 (mcg 100) | 0.133 |
| Example 2 | |
| Hylon VII | 36 |
| Glycerin 85% | 36 |
| Xantan gum | 0.35 |
| Water | 27.517 |
| T4 (mcg 100) | 0.133 |
| Example 3 | |
| Hylon VII | 28 |
| Lycoat RS 780 | 10 |
| Glycerin 85% | 36 |
| Xantan gum | 0.3 |
| Water | 25.567 |
| T4 | 0.133 |

|  | % w/w |
|---|---|
| Example 4 | |
| Hylon VII | 23 |
| Lycoat RS 780 | 15 |
| Glycerin 85% | 36 |
| Xantan gum | 0.3 |
| Water | 25.567 |
| T4 | 0.133 |
| Example 5 | |
| Hylon VII | 28 |
| Lycoat RS 780 | 10 |
| Glycerin 85% | 36 |
| Carra Sol CPA 5919 | 0.3 |
| Water | 25.567 |
| T4 (mcg 100) | 0.133 |
| Example 6 | |
| Hylon VII | 15 |
| Lycoat RS 780 | 23 |
| Glycerin 85% | 36 |
| Carra Sol CPA 5919 | 0.3 |
| Water | 25.567 |
| T4 (mcg 100) | 0.133 |
| Example 7 | |
| Hylon VII | 15 |
| Lycoat RS 780 | 23 |
| Glycerin 85% | 36 |
| Xantan gum | 0.05 |
| Water | 25.817 |
| I fill moT4 (mcg 100) | 0.133 |
| Example 8 | |
| Hylon VII | 41 |
| Glycerin 85% | 25 |
| Xantan gum | 0.15 |
| Water | 33.717 |
| T4 (mcg 100) | 0.133 |

The invention claimed is:

1. A soft capsule comprising:
an interior fill,
wherein said fill comprises one or more thyroid hormones and a high-amylose starch,
wherein said high-amylose starch comprises between 50 and 85% by weight of amylose with respect to the total weight of the starch.

2. The soft capsule according to claim 1, wherein the amount of high-amylose starch is between 10 and 50% by weight based on the weight of the fill.

3. The soft capsule according to claim 2, wherein the amount of high-amylose starch is between 15 and 45% by weight based on the weight of the fill.

4. The soft capsule according to claim 1, wherein said fill further comprises one or more vegetable hydrocolloids.

5. The soft capsule according to claim 4, wherein the vegetable hydrocolloid is selected from the group consisting of xanthan, carrageenan, and mixtures thereof.

6. The soft capsule according to claim 5, wherein the vegetable hydrocolloid comprises carrageenan in the range of 0.05-5% by weight based on the weight of the fill.

7. The soft capsule according to claim 6, wherein the vegetable hydrocolloid comprises carrageenan in the range of 0.2-3% by weight based on the weight of the fill.

8. The soft capsule according to claim 4 wherein the vegetable hydrocolloid comprises xanthan in the range of 0.03-3% by weight based on the weight of the fill.

9. The soft capsule according to claim 8, wherein the vegetable hydrocolloid comprises xanthan in the range of 0.05-2% by weight based on the weight of the fill.

10. The soft capsule according to claim 1, wherein said fill comprises glycerol.

11. The soft capsule according to claim 10, wherein glycerol is in the range of 12-45% by weight based on the weight of the fill.

12. The soft capsule according to claim 11, wherein glycerol is in the range of 20-40% by weight based on the weight of the fill.

13. A process for preparing a soft capsule provided with a capsular wall and a fill, comprising: preparing a composition of a fill, wherein said fill comprises one or more thyroid hormones and a high-amylose starch, wherein said high-amylose starch comprises between 50 and 85% by weight of amylose with respect to the total weight of the starch, dividing said composition into discrete units, coating said units with a solution of the components of the capsular wall, drying the resulting product.

14. A method for treating and/or preventing diseases and/or physiological conditions requiring the administration of thyroid hormones, comprising administering a soft capsule of claim 1 to a patient in need thereof.

15. The soft capsule according to claim 1, wherein said high-amylose starch in the fill increases storage stability of the one or more thyroid hormones as compared to a standard starch having an amylose content of less than 30%.

16. The soft capsule according to claim 15, wherein the one or more thyroid hormones are thyroxine, triiodothyronine, and combinations thereof.

* * * * *